United States Patent [19]

Wenten et al.

[11] Patent Number: 5,560,828

[45] Date of Patent: Oct. 1, 1996

[54] METHOD FOR THE REMOVAL OF COMPONENTS CAUSING TURBIDITY, FROM A FLUID, BY MEANS OF MICROFILTRATION

[75] Inventors: Gede Wenten, Bali, Indonesia; Dirk M. Koenhen, Dedemsvaart; Hendrik D. W. Roesink, Borne, both of Netherlands; Alan Rasmussen, Charlottenlund; Gunnar Jonsson, Vaerlose, both of Denmark

[73] Assignee: X-Flow B.V., Almelo, Netherlands

[21] Appl. No.: 312,481

[22] Filed: Sep. 23, 1994

[30] Foreign Application Priority Data

Sep. 24, 1993 [NL] Netherlands ............... 9301653

[51] Int. Cl.$^6$ ................... B01D 61/00; B01D 65/02
[52] U.S. Cl. ............... 210/651; 210/650; 210/636; 210/333.1; 210/333.01; 210/108
[58] Field of Search .................. 210/650, 651, 210/636, 791, 333.01, 333.1, 108, 490

[56] References Cited

U.S. PATENT DOCUMENTS

| Re. 34,296 | 6/1993 | Roesink | 210/900 |
|---|---|---|---|
| 4,333,972 | 6/1982 | Kesting | 427/244 |
| 4,340,479 | 7/1982 | Pall | 210/490 |
| 4,629,563 | 12/1986 | Wrasidlo | 210/500.34 |
| 4,897,465 | 1/1990 | Cordle et al. | 210/650 |
| 4,983,288 | 1/1991 | Karbachsch et al. | 210/321.87 |
| 5,064,580 | 11/1991 | Beck et al. | 210/500.27 |
| 5,076,925 | 12/1991 | Roesink et al. | 210/500.23 |
| 5,221,479 | 6/1993 | Etoh et al. | 210/636 |
| 5,344,565 | 9/1994 | Degeh et al. | 210/636 |

FOREIGN PATENT DOCUMENTS

| 4105210 | 3/1992 | Germany. |
|---|---|---|
| 4204708 | 8/1992 | Germany. |
| 2219221 | 12/1989 | United Kingdom. |

OTHER PUBLICATIONS

"Polarization Control With Backwashing" Handbook Separation Techniques For Chemical Engineers, Philip A. Schweitzer, pp. 2-30-2-32.
Sasacki, Patent Abtracts of Japan; Microporous Membrane, vol. 11 No. 202, Jun. 30, 1987.

*Primary Examiner*—Ana Fortuna
*Attorney, Agent, or Firm*—Wolf, Greenfield & Sacks, P.C.

[57] ABSTRACT

The invention relates to a process for the removal of components causing turbidity, from a fluid, by means of microfiltration, whereby the fluid is beer, wine, fruit juice, bacterial suspension, blood, milk, enzyme suspension, etc. According to the invention, the fluid to be treated is fed across an asymmetric membrane having a pore structure such that the pores on the feed side of the membrane are larger than the nominal pore size and the pores of nominal pore size occur in the cross section toward the permeate side, the filtered off components are back-flushed from the membrane and are subsequently carried away with the fluid. The nominal pore size is usually 0.1–5.0 μm and preferably 0.2–1.0 μm. The membrane may be tubular, flat or capillary. Back-flushing takes place intermittently with a frequency of 1 second to 10 minutes for 0.1–1 second at a counter pressure of 0.5–5 bar. The feed velocity is preferably below 2 m/s and the pressure difference over the membrane is less than 0.5 bar.

15 Claims, No Drawings

METHOD FOR THE REMOVAL OF COMPONENTS CAUSING TURBIDITY, FROM A FLUID, BY MEANS OF MICROFILTRATION

FIELD OF THE INVENTION

The present invention relates to a method for the removal of components that cause turbidity, from a fluid, by means of microfiltration.

The application of microfiltration whereby by maintaining a flow along the membrane wall, it is attempted to prevent accumulation of dirt, is a known technique. This technique is generally called cross flow microfiltration.

In practice, this technique is applied in, for instance, ultrafiltration and microfiltration.

Effective velocities to prevent the build-up of a fouling layer often begin at 2 m/s while as a rule velocities from 4–6 m/s are used.

Dependent on the membrane configuration, this is the range where turbulence in the flow occurs.

It should be noted that the technique of back-flushing membranes was introduced by Klein and Schneider for self-supporting capillary membranes (Desalination 41 (1982 263–275) whereby microfiltration membranes were applied with a pore size of above 0.01 µm. For further prior art, reference is made to "Microfiltration mir Membranen" by S. Ripperger (ISBN 3-527-28457-5, 1992).

In the above-mentioned known techniques the back-flush is performed once every few minutes, giving a loss of production because part of the permeate is pushed back to the concentrate side of the membrane. A special technique is used by Memtec, who back-flush the membrane with gas (AU-B-34,400/84). The fastest back-flush intervals are recorded in DK-A-476/90 (APV Pasilac).

Here back-flush frequencies are recorded of 1–10 back-flushes per minute at a back-flush duration of 1–5 seconds. One thing and another results in the fact, that due to these relative long back-flushing times the installation is not in use for filtration for 10–20% of the time.

A disadvantage of the known membrane is that it suffers a productivity drop due to the formation of a so-called secondary membrane, consisting of a packing of particles to be filtered off, which partly plug the pores and as layer shows only a limited "own" permeability.

The object of the invention is to provide a method with practically no productivity drop because the thickness of the layer of particles to be filtered off is limited and the secondary membrane is disturbed.

To this end, the present invention provides a method for the removal of components causing turbidity from a fluid, by means of microfiltration, characterized in that the fluid flows over an asymmetric membrane having a membrane structure such that the pores on the feed side of the membrane are larger than the nominal pore size and the pores having a nominal pore size are located in the cross section toward the permeate side, the filtered off components are back-flushed from the membrane and are subsequently carried away with the fluid.

In such an asymmetric membrane according to the invention the pores on the feed side of the membrane are larger than the nominal pore size.

The method according to the invention is especially suitable for the removal of components causing turbidity from beer, wine, fruit juice, bacterial suspension, blood, milk, enzyme suspension, etc.

As fruit juice are considered: cherry juice, apple juice, etc.

The present invention has been shown to be especially suitable for the treatment of beer, yielding a particularly clear beer, which beer in addition remains stable during a long storage time.

The asymmetric membrane used is preferably a membrane having a nominal pore size of 0.1–5.0 µm.

A membrane having a nominal pore size of 0.2–1.0 µm has proved to be especially suitable. Membranes which according to the invention meet the requirements very well are tubular, flat or capillary.

In the method according to the invention membranes are used that reject certain components, while in many cases it is of great importance that some other components will permeate through the membrane. This is especially important, for instance, for the clarification of beer. As already known, in the production of beer yeast is used, making the beer turbid, which is the reason why after the process the yeast must be removed from the beer. Apart from yeast the beer also contains precipitated proteins, which are also components responsible for poor beer quality. On the other hand, beer also contains components that must not be removed during filtration, which components are high molecular weight components attributing to the beer's taste, color, foam stability, etc. Of course, the same also goes for wine and other fruit juices.

It is especially very important that the high molecular weight colloidal components permeate through during filtration of the fluid.

Surprisingly it was found, that the use of hydrophilic membranes of the type described in the U.S. patent RE 34296 and U.S. Pat. No. 5,076,925 give excellent results. Naturally, the invention is not limited to the above-mentioned membranes.

It has been shown that when using the method according to the invention particularly good results are obtained when the asymmetric membrane is intermittently back-flushed with a frequency of 1 second to 10 minutes for 0.1–1 second at a counter pressure of 0.5–5 bar.

Intermittent back-flushing of the membrane can, for instance be realized by means of an electronic three-way valve, entirely controlled by computer. The back-flush medium used here is compressed air. Apart from compressed air other suitable back-flush mediums may be used.

Good results are obtained when the fluid to be treated is brought in with a flow velocity below 2 m/s .

Surprisingly it was found, that the method according to the invention can be applied successfully if the pressure difference over the membrane is less than 0.5 bar.

The invention will now be further elucidated by means of the following, non-limitative examples.

In Example I and II, standard technology asymmetric ceramic membranes are used, whereby there is no back-flushing in Example I. In Example II, back-flushing does take place.

Examples III to IX relate to beer filtration using an asymmetric membrane according to the invention, while Examples X and XI relate to cherry juice filtration, also using an asymmetric membrane according to the invention.

EXAMPLE I

Unfiltered Carlsberg pilsner beer was subjected to filtration using an asymmetric ceramic membrane, whereby no back-flushing was carried out.

This ceramic membrane has a nominal pore size of 1.0 μm. The beer was supplied with a cross flow velocity of 0.5 m/s. The pressure difference over the membrane was 0.15 bar. Within 2 hours the flux of the membrane appeared to decline from 150 to 3 $l/m^2/h$. This rapid flux decline renders such a filtration system without back-flush unsuitable for beer filtration.

EXAMPLE II

Again, unfiltered Carlsberg pilsner beer was filtered using an asymmetric ceramic membrane, whereby back-flushing did take place.

The nominal pore size, cross flow velocity and pressure differences over the membrane are the same as in Example I. Back-flushing was carried out with an interval of 3 seconds, whereby each back-flush lasted 0.05 seconds. By using the same membrane as in Example I, but with back-flushing, the flux was shown to decline in 2 hours from 150 to 70 $l/m^2/h$. This demonstrates clearly the favorable effect of back-flushing on the flux.

EXAMPLE III

Unfiltered Carlsberg pilsner beer was filtered using an asymmetric (X-Flow) membrane, however, without back-flushing.

The nominal pore size of the used asymmetric membrane was 0.66 μm, while the beer was supplied with a velocity of 0.5 m/s.

The pressure differences over the membrane was 1.0 bar. After 6 hours the flux was shown to have declined from 180 to 18 $l/m^2/h$. 75% of proteins of high molecular weight were seen to have permeated.

EXAMPLE IV

Unfiltered Carlsberg pilsner beer was filtered using an asymmetric (X-Flow) membrane.

The nominal pore size of the membrane was 0.66 μm, while the beer was supplied with a velocity of 0.5 m/s.

The pressure difference over the membrane was 0.05 bar.

Back-flushing was carried out at an interval of 1 minute, while each back-flush lasted 5 seconds.

After 3 hours the flux was shown to have declined from 120 to 108 $l/m^2/h$.

EXAMPLE V

Unfiltered Carlsberg pilsner beer was filtered using an asymmetric (X-Flow) membrane, with back-flushing.

The pore size was 0.66 μm, while the beer was supplied with a velocity of 0.5 m/s.

The pressure difference over the membrane was 0.05 bar.

Back-flushing was carried out every 3 seconds, while each back-flush lasted 0.05 seconds. Surprisingly, it was shown that the flux remained constant for 3 days, at 120 $l/m^2/h$, 100% of the proteins of high molecular weight had permeated.

EXAMPLE VI 400 liters beer containing yeast rests (unfiltered Carlsberg pilsner) were filtered. It took 124 minutes to obtain 300 liters permeate. The membrane surface measured 1 $m^2$ and the transmembrane pressure, the feed pressure was 0.04 to 0.08 bar, productivity was maintained around 150 $l/m^2/h$. The crossflow velocity was 0.5 m/s.

Every 5 seconds a back-flush pulse was given with a pressure of about 1.5 bar lasting less than 0.1 second. The temperature of the beer was 0° C. The nominal pore size of the membrane was 0.6 μm.

The data show that high velocity back-flushing has a tremendously good effect on the constancy of the membrane productivity. In standardized figures, this is 1875 $l/m^2/h/bar$.

EXAMPLE VII

The membrane of Example VI was applied with a nominal pore size of 0.6 μm.

In a similar experiment using a cross flow velocity of 2.3 m/s and a pressure of 2 bar an average flux of 80 $l/m^2/h$ was achieved without back-flushing, but under otherwise the same conditions. Standardized this means a productivity of 40.

EXAMPLE VIII

In this Example, the same membrane was used as in Examples VI and VII.

In the same situation as above, a flux was obtained of 30 $l/m^2/h/bar$.

EXAMPLE IX

In this Example, the same membrane was used as in Examples VI and VII.

By back-flushing in the conventional manner every 5 minutes for 5 seconds, a flux was obtained of 80 $l/m^2/h/bar$.

EXAMPLE X

This Example relates to the filtration of cherry juice using an asymmetric (X-Flow) membrane without back-flushing.

The nominal pore size of the membrane was 0.51 μm, while the cherry juice was supplied with a velocity of 0.5 m/s.

The pressure difference over the membrane was 0.5. After 2 hours the flux was shown to decline from 120 to 5 $l/m^2/h$.

EXAMPLE XI

Cherry juice was filtered by means of an asymmetric (X-Flow) membrane as in Example X, but with back-flushing.

The nominal pore size of the membrane was 0.51 μm, while the cherry juice was supplied with a velocity of 0.5 m/s.

The pressure difference over the membrane was 0.5. Back-flushing took place every 3 seconds, every time flushing for 0.05 seconds.

After 2 hours, the flux was shown to have declined from 120 to 80 $l/m^2/h$.

What is claimed is:

1. A process for the removal of components causing turbidity, from a feed fluid, by means of microfiltration, comprising:

feeding the feed fluid across and parallel to a feed side wall of an asymmetric membrane, wherein the pores on the feed side wall of the membranes are larger than the nominal pore size and the pores of nominal pore size occur in the cross section toward the permeate side of the membrane;

back-flushing the components causing turbidity from the feed side wall of the membrane; allowing the components causing turbidity to be carried away with the feed fluid, wherein allowing the components causing turbidity to be carried away with the feed fluid, wherein the back-flushing of the membrane is performed intermittently with a frequency of 1 second to 10 minutes for 0.1–1 second at a counter pressure of 0.5–5 bar, maintaining a constant membrane flux.

2. A process according to claim 1, wherein the feed fluid is selected from the group consisting of beer, wine, fruit juice, bacterial suspension, blood, milk, and enzyme suspension.

3. A process according to claim 1 or 2 wherein the feed fluid is beer.

4. A process according to claim 1 or 2, wherein the asymmetric membrane comprises a microporous membrane having a nominal pore size of 0.1–5.0 μm.

5. A process according to claim 4, wherein the nominal pore size is 0.2–1.0 μm.

6. A process according to claim 4, wherein the feed fluid is beer.

7. A process according to claim 1 or 2, wherein the membrane is selected from the group consisting of a tubular membrane, a flat membrane and a capillary membrane.

8. A process according to claim 7, wherein the feed fluid is beer.

9. A process according to claim 1 or 2, wherein the feed fluid velocity is below 2 m/s.

10. A process according to claim 9, wherein the feed fluid is beer.

11. A process according to claim 1 or 2, wherein the pressure difference across the membrane is less than 0.5 bar.

12. A process according to claim 11, wherein the feed fluid is beer.

13. A process according to claim 1 or 2, wherein the asymmetric membrane comprises a microporous membrane having a nominal pore size of 0.1–5.0 μm, wherein the membrane is selected from the group consisting of a tubular membrane, a flat membrane and a capillary membrane, and wherein the feed fluid velocity is below 2 m/s.

14. A process for the removal of components causing turbidity, from a feed fluid, by means of microfiltration, comprising:

feeding the feed fluid across and parallel to a feed side wall of an asymmetric membrane, wherein the pores on the feed side wall of the membrane are larger than the nominal pore size and the pores of nominal pore size occur in the cross section toward the permeate side of the membrane;

back-flushing the components causing turbidity from the feed side wall of the membrane; and allowing the components causing turbidity to be carried away with the feed fluid, wherein the back-flushing of the membrane is performed intermittently with a frequency of 1 second to 10 minutes for less than 1 second.

15. A process according to claim 14, wherein the feed fluid is selected from the group consisting of beer, wine, fruit juice, bacterial suspensions, blood, milk and enzyme suspensions.

* * * * *